(12) United States Patent
Wang et al.

(10) Patent No.: US 12,419,724 B2
(45) Date of Patent: Sep. 23, 2025

(54) ORAL DIGITAL IMPRESSION INSTRUMENT, DIGITAL MODEL FOR THE SAME, AND INTELLIGENT METHOD OF MAKING AND/OR USING THE SAME

(71) Applicant: ChengDu Besmile Medical Technology Corp. Ltd., Chengdu (CN)

(72) Inventors: Changjian Wang, Chengdu (CN); Dengkai Zhang, Chengdu (CN); Xinzhang Yan, Chengdu (CN); Guanghui Lu, Chengdu (CN); Hongbin Cai, Chengdu (CN)

(73) Assignee: CHENGDU BESMILE MEDICAL TECHNOLOGY CORP. LTD., Chengdu (CN)

( * ) Notice: Subject to any disclaimer, the term of this patent is extended or adjusted under 35 U.S.C. 154(b) by 557 days.

(21) Appl. No.: 18/048,650

(22) Filed: Oct. 21, 2022

(65) Prior Publication Data
US 2023/0113425 A1    Apr. 13, 2023

Related U.S. Application Data

(63) Continuation of application No. PCT/CN2021/218724, filed on Apr. 21, 2021.

(30) Foreign Application Priority Data

Apr. 30, 2020    (CN) .......................... 202010360675.2

(51) Int. Cl.
*A61C 7/00*      (2006.01)
*A61C 5/70*      (2017.01)
(Continued)

(52) U.S. Cl.
CPC ................ *A61C 7/002* (2013.01); *A61C 5/70* (2017.02); *A61C 5/77* (2017.02); *A61C 9/004* (2013.01);
(Continued)

(58) Field of Classification Search
CPC ... A61C 7/002; A61C 13/0004; A61C 9/0053; A61C 5/77; A61C 19/04; A61C 9/004;
(Continued)

(56) References Cited

U.S. PATENT DOCUMENTS

| 10,258,439 B1* | 4/2019 | Kitching ................ A61C 7/002 |
| 2007/0128573 A1* | 6/2007 | Kuo ........................ A61C 7/08 |
| | | 433/24 |

(Continued)

FOREIGN PATENT DOCUMENTS

| CN | 101548911 A | 10/2009 |
| CN | 107230255 A | 3/2017 |

(Continued)

OTHER PUBLICATIONS

International Search Report; International Searching Authority/CN dated Jul. 21, 2021; International Application No. PCT/CN2021/088569; 3 pgs.; National Intellectual Property Administration, PRC (ISA/CN); Beijing, China.

*Primary Examiner* — Sumati Lefkowitz
*Assistant Examiner* — Ryan P Potts
(74) *Attorney, Agent, or Firm* — Central California IP Group, P.C.; Andrew D. Fortney

(57) ABSTRACT

An oral digital impression instrument that includes a set of computer-readable instructions configured to implement an intelligent design method of a digital model. The method includes the steps of data acquisition, data preprocessing, intelligent design, alternative dental crown matching, dental pattern adjustment and the like. A to-be-produced tooth is produced through extracting a distance between teeth adjacent to the to-be-produced tooth, buccal and lingual dental arch crown curves, an occlusal gum diameter height and cusp pit and fissure ridge shape features of opposite jaws, and matching and adjusting alternative dental crown models.

18 Claims, 3 Drawing Sheets

(51) Int. Cl.
  *A61C 5/77*   (2017.01)
  *A61C 9/00*   (2006.01)
  *A61C 13/00*  (2006.01)
  *A61C 13/08*  (2006.01)
  *A61C 19/04*  (2006.01)
  *G06F 30/00*  (2020.01)
  *G06T 7/00*   (2017.01)
  *G16H 30/40*  (2018.01)

(52) U.S. Cl.
  CPC .......... *A61C 13/0004* (2013.01); *A61C 13/08* (2013.01); *A61C 19/04* (2013.01); *G06F 30/00* (2020.01); *G06T 7/0012* (2013.01); *G16H 30/40* (2018.01); *A61C 9/0053* (2013.01); *G06T 2207/30036* (2013.01)

(58) Field of Classification Search
  CPC ......... A61C 9/0046; A61C 13/08; A61C 5/70; A61C 13/0006; A61C 13/00; A61C 19/05; A61C 8/0036; G06T 2207/30036; G06T 17/00; G06T 15/08; G06T 7/0012; G16H 30/40; G06F 30/00; G06F 30/12
  See application file for complete search history.

(56) References Cited

U.S. PATENT DOCUMENTS

| | | | |
|---|---|---|---|
| 2011/0196524 A1* | 8/2011 | Giasson | B33Y 50/00 700/118 |
| 2014/0294273 A1* | 10/2014 | Jaisson | A61B 5/0035 382/131 |
| 2018/0005371 A1* | 1/2018 | Sabina | A61C 9/0046 |
| 2020/0005552 A1* | 1/2020 | Furst | G06V 10/751 |

FOREIGN PATENT DOCUMENTS

| | | | | |
|---|---|---|---|---|
| CN | 107019570 A | | 8/2017 | |
| CN | 106504331 A | | 9/2017 | |
| CN | 107644685 A | * | 1/2018 | |
| CN | 110025387 A | | 7/2019 | |
| JP | 2000107203 A | | 4/2000 | |
| WO | WO-2009035142 A1 | * | 3/2009 | ............... A61C 5/77 |

* cited by examiner

ORAL DIGITAL IMPRESSION INSTRUMENT, DIGITAL MODEL FOR THE SAME, AND INTELLIGENT METHOD OF MAKING AND/OR USING THE SAME

CROSS REFERENCE TO RELATED APPLICATION(S)

This application is a continuation of International Pat. Appl. No. PCT/CN2021/218724, filed on Apr. 21, 2021, pending, which claims the benefit of Chinese Patent Application No. 202010360675.2, filed on Apr. 30, 2020, each of which is incorporated herein by reference as if fully set forth herein.

FIELD OF THE INVENTION

The present invention relates to the technical field of medical computer aided design, and particularly to an intelligent design method of a digital model for an oral digital impression instrument, and the oral digital impression instrument.

DISCUSSION OF THE BACKGROUND

When producing dental implants in the oral cavity or oral rehabilitation traditionally, dentists usually use intraoral scanners to scan the patient's oral cavity to obtain the 3D model data of the teeth in the oral cavity, and then transmit them to professional design factories for design and processing. Professional design factories also need to design manually according to the design requirements proposed by dentists and their own design experience; however, this traditional semi-manual design method is time-consuming, inefficient, and has a long production period. In addition, the designers in the factory do not directly contact the patients, so it is difficult to adjust the standard teeth to the optimal size and pattern. As a result, the fabricated teeth cannot be suitable for the patients. After installation, dentists need to make subsequent adjustments.

SUMMARY OF THE INVENTION

In order to solve the above problem, the present invention provides an intelligent design method of a digital model for an oral digital impression instrument, and an oral digital impression instrument able to implement the intelligent design method and the digital model.

In order to achieve the above purpose, the technical solution adopted in the present invention is as follows: the method comprises the following steps:
1) database establishment: tooth data being stored in an xml file, and stored alternative dental crown data information including a tooth number, a dental crown type as a single crown or crown bridge, an overall size feature vector of a dental crown, and a storage path of a tooth;
2) data acquisition: acquiring 3D model data of an oral cavity model after tooth preparation with oral digital acquisition equipment, the data acquired by the oral digital acquisition equipment including an upper jaw and a lower jaw, as well as confirming occluding relations between the upper jaw and the lower jaw;
3) data preprocessing: labeling the 3D model of the oral cavity obtained in step 2), and labeling an abutment tooth position, single crown/crown bridge and an abutment edge line;
4) intelligent design: performing automatic design processing on a to-be-produced tooth according to the 3D model obtained by the preprocessing in step 3), and matching several alternative dental crowns from the database;
5) alternative dental crown matching: determining the similarity between the alternative dental crown and the to-be-produced tooth according to the cosine of an included angle between the overall size feature vector of the dental crown of the alternative dental crown and the overall size feature vector of the dental crown of the to-be-produced tooth, the cosine of the included angle being [0, 1];
6) dental pattern adjustment: adjusting according to the scaling of the overall size feature vector of the to-be-produced tooth, a maxillofacial feature vector and the alternative dental crown;
7) data output: the designed tooth model being exported as a data format which can be imported by 3shape and EXOcad software.

Preferably, the overall size feature vector of the dental crown in step 1) is (size_x, size_y, size_z), which is obtained through calculation by a six-point method, and the six-point method obtains six outline high points through the maximum and minimum tooth crown coordinates, of which two outline high points of the mesial and distal surfaces are $P_{min}^{x}$ and $P_{max}^{x}$, two outline high points of the buccal and lingual surfaces are $P_{min}^{y}$ and $P_{max}^{y}$, and two outline high points of the bottom and top surfaces are $P_{min}^{z}$ and $P_{max}^{z}$; size_x is the absolute value of the difference between x coordinates of the outline high points $P_{min}^{x}$ and $P_{max}^{x}$, size_y is the absolute value of the difference between y coordinates of the outline high points $P_{min}^{y}$ and $P_{max}^{y}$, and size z is the absolute value of the difference between z coordinates of the outline high points $P_{min}^{z}$ and $P_{max}^{z}$.

Preferably, data acquisition in step 2) comprises the following steps:
2.1) acquiring 3D model data of the upper jaw and the lower jaw and buccal data at occlusion respectively; and
2.2) calculating and fixing the contact relation between the 3D models of the upper jaw and the lower jaw through buccal data, or manually translating and rotating the 3D models of the upper jaw and the lower jaw in the 3D coordinate system, so that the 3D models of the upper jaw and the lower jaw are in a correct occluding relation.

Preferably, data preprocessing in step 3) comprises the following steps:
3.1) selecting the abutment after tooth preparation, highlighting it, and recording the tooth number of the tooth position, the tooth number rule of the tooth position being given by the Federation Dentaire Internationale (FDI) notation;
3.2) selecting the type of the abutment as a single crown or a crown bridge: if it is a single crown, recording the tooth number of the abutment; if it is a crown bridge, recording the tooth numbers of the leftmost and rightmost abutments of the crown bridge and the tooth numbers of all to-be-produced teeth; and
3.3) marking the edge lines interactively, selecting the points of triangular mesh on the edge line of the abutment, sketching the points of the abutment edge line one by one, and completing the selection of the abutment edge line; and highlighting the final edge line with a special color.

Preferably, intelligent design in step 4) comprises the following steps:

3.1) calculating the distance between adjacent teeth: interactively selecting the two points closest to the adjacent teeth on the abutment edge line, and calculating the distance between these two points to obtain the distance between adjacent teeth;

3.2) calculating the buccal and lingual dental arch convexity curves: fitting the dental arch convexity curve by a β function-based method according to the 3D model data of the upper jaw and the lower jaw obtained in step 2);

3.3) calculating the occlusal gum diameter height: calculating the distance from each point on the abutment edge line to the occlusal plane according to the selected abutment edge line, and calculating the average distance as the occlusal gum diameter height;

3.4) calculating the cusp pit and fissure ridge shape features of opposite jaws: calculating the occlusal surface features of the opposite jaw tooth according to the 3D model data of the upper jaw and lower jaw obtained in step 2).

Preferably, step 3.2) comprises the following steps:

3.2.1) obtaining the buccal apex of incisor contact surface of the jaw where the abutment is, the point of bilateral canines with the maximum buccal curvature, and the point of bilateral second permanent molars with the maximum buccal curvature;

3.2.2) determining the β function according to the points (which may be 5 points or more) obtained in step 3.2.1) to fit a dental arch convexity curve (e.g., the buccal dental arch convexity curve);

3.2.3) repeating steps 3.2.1) and 3.2.2), and calculating the lingual dental arch convexity curve in the same manner.

Preferably, step 3.4) comprises the following steps:

3.4.1) interactively selecting the occlusal surface of the opposite jaw tooth;

3.4.2) calculating the feature vector of the selected occlusal surface: first, obtaining the effective neighborhood around the cusp pit and fissure ridge in the occlusal surface according to the selection results, then establishing a local spherical coordinate system for the surface, next, calculating the elevation and azimuth of the normal at each vertex of the surface through the 2D histogram statistical method, and determining the position index in turn; finally, generating the maxillofacial feature vector (f1, f2, ..., fn) of the opposite jaw tooth according to the 2D histogram.

Preferably, alternative dental crown matching in step 5) comprises the following steps:

4.1) tooth number and tooth type matching: finding out alternative dental crown data in the database according to the tooth number of the selected abutment and the dental crown type selected as single crown or crown bridge;

4.2) overall size matching: calculating the overall size feature vector of the dental crown of the to-be-produced tooth as (size_$x_0$, size_$y_0$, size_$z_0$) and the overall size feature vector of the dental crown of the alternative dental crown as (size_x', size_y', size_z'), and determining the similarity between the alternative dental crown and the to-be-produced tooth according to the cosine between the overall size feature vector of the dental crown of the alternative dental crown and the overall size feature vector of the dental crown of the to-be-produced tooth; the larger the cosine of the included angle, the smaller the included angle of the two vectors; when the directions of the two vectors coincide, the maximum cosine of the included angle is 1;

4.3) local feature matching: calculating the complementary vector (f1', f2', ..., fn') of the maxillofacial feature vector (f1, f2, ..., fn) of the opposite jaw tooth of the to-be-produced tooth, the complementary vector (f1', f2', ..., fn')=(−f1, −f2, ..., −fn), and conducting local feature matching through calculating the cosine similarity of the vector (f1', f2', ..., fn') and the maxillofacial feature vector (F1, F2, ..., Fn) of the alternative dental crown.

Preferably, dental pattern adjustment in step 6) comprises the following steps:

5.1) integral adjustment: adjusting by virtue of scaling matrix S according to the overall size feature vector of the to-be-produced tooth and the scaling of the alternative dental crown, in order to ensure the best size matching of the alternative dental crown;

5.2) occlusal surface adjustment: adjusting the normal vector of the dental surface of the alternative dental crown according to the maxillofacial feature vector of the opposite jaw tooth of the to-be-produced tooth to best fit;

5.3) adjusting the lower edge of the dental crown, adjusting the coordinates of each point on the lower edge of the alternative dental crown according to the distance from each point on the abutment edge line to the occlusal plane calculated in step 3.3), so that the distance from the each point on the lower edge of the alternative dental crown to the highest point on the occlusal surface matches the distance from each point on the abutment edge line to the occlusal plane.

The method may model and/or design a dental crown and/or a to-be-produced tooth using the oral digital impression instrument, and may be part of another method to make the dental crown and/or the produced tooth, and place the dental crown and/or the produced tooth in a patient's oral cavity. The oral digital impression instrument comprises oral digital acquisition equipment, such as an intraoral scanner, configured to scan an oral cavity of a patient and obtain three-dimensional (3D) data of teeth in the oral cavity, and a computer comprising a processor, a memory, a display (e.g., adapted to display the models generated by the present method and/or set of instructions) and an input or interface device, the memory storing therein a non-transitory set of instructions which, when executed by the processor, is configured to implement the intelligent method. The intelligent design method, digital oral model and oral digital impression instrument may be adapted for use beside or in proximity to a dental chair.

The present invention has the following advantages that: through computer aided design, several matching alternative dental crowns can be quickly retrieved from the database, and the most suitable alternative dental crowns can be determined by the similarity of the overall size feature vectors of the to-be-produced tooth and the alternative dental crown; The design method can produce to-be-produced teeth with high precision and efficiency, accelerate the denture processing speed, reduce the intermediate links of processing, and change the clinical work process and communication between doctors and patients.

DETAILED DESCRIPTION

The present invention belongs to the technical field of medical computer aided design technology, and particularly to an intelligent design method of a digital model for an oral digital impression instrument. Based on oral digital acquisition equipment, such as oral digital impression instrument, the present invention provides an intelligent tooth design technology, which can intelligently generate teeth by calculating various quantitative data after tooth preparation in a virtual 3D environment.

Figure 1:
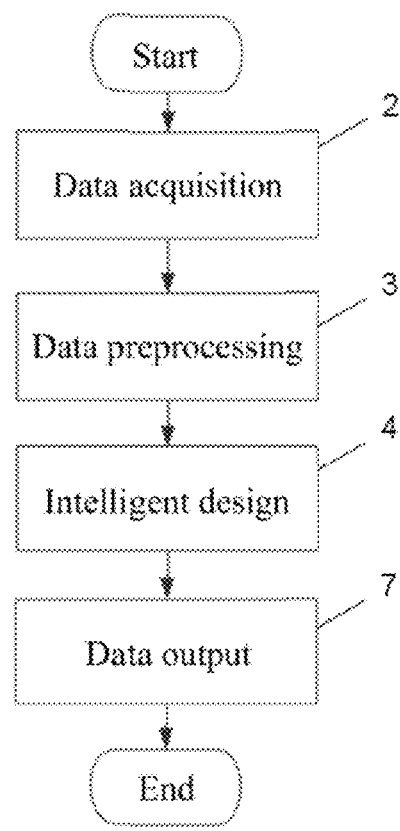
FIG. 1 is the flow chart of an intelligent design technology for a digital oral model of the present invention.

The flow chart as shown in FIG. 1 illustrates the specific process of the entire implementation of the present invention:

Data acquisition 2: acquiring 3D model data of an oral cavity model after tooth preparation with oral digital acquisition equipment, the data acquired by the oral digital acquisition equipment including an upper jaw and a lower jaw, as well as confirming occluding relations between the upper jaw and the lower jaw.

This step mainly comprises the following steps:

2.1) acquiring 3D model data of the upper jaw and the lower jaw and buccal data at occlusion, respectively; and 2.2) calculating and fixing the contact relation between the 3D model of the upper (lower) jaw through buccal data, or manually translating and rotating the 3D model of the lower (upper) jaw in the 3D coordinate system, so that the 3D models of the upper jaw and the lower jaw are in a correct occluding relation.

Data preprocessing 3: first labeling the 3D model of the oral cavity obtained in step 2, and labeling an abutment tooth position, single crown/crown bridge and an abutment edge line.

This step mainly comprises the following steps:

3.1) selecting the abutment after tooth preparation, highlighting it, and recording the tooth number of the tooth position(s), the tooth numbering rule of the tooth position(s) being given or defined by the FDI notation;

3.2) selecting the type of the abutment (single crown or crown bridge): if it is a single crown, recording the tooth number of the abutment; if it is a crown bridge, recording the tooth numbers of the leftmost and rightmost abutments of the crown bridge and the tooth numbers of all to-be-produced teeth; and 3.3) marking the edge lines interactively: clicking on or selecting the points of triangular mesh on the edge line of the abutment with a mouse or other human input or interface device (HID) operatively connected to the computer, sketching the points of the abutment edge line one by one, and if necessary completing the selection of the abutment edge line; during the sketching process, the 3D model of the jaw can be translated or rotated (e.g., on the display) to avoid incomplete occlusion; and highlighting the final edge line, for example with a special color.

Intelligent design 4: automatically designing the produced teeth according to the 3D model data obtained in step 3.

This step mainly comprises the following steps:

4.1) calculating the distance between adjacent teeth: interactively selecting the two points closest to the adjacent teeth on the abutment edge line, and calculating the distance between these two points to obtain the distance between adjacent teeth, the specific calculation formula being shown as formula (1):

$$d=\sqrt{(x_2-x_1)^2+(y_2-y_1)^2+(z_2-z_1)^2} \quad \text{Formula (1)}$$

where, $(x_2, y_2, z_2)$, $z_1$) are the 3D coordinates of two points on the abutment; and 4.2) calculating the buccal and lingual dental arch convexity curves: fitting the dental arch convexity curve by a β function-based method according to the 3D model data of the upper jaw and the lower jaw obtained in step 2.

Figure 2:
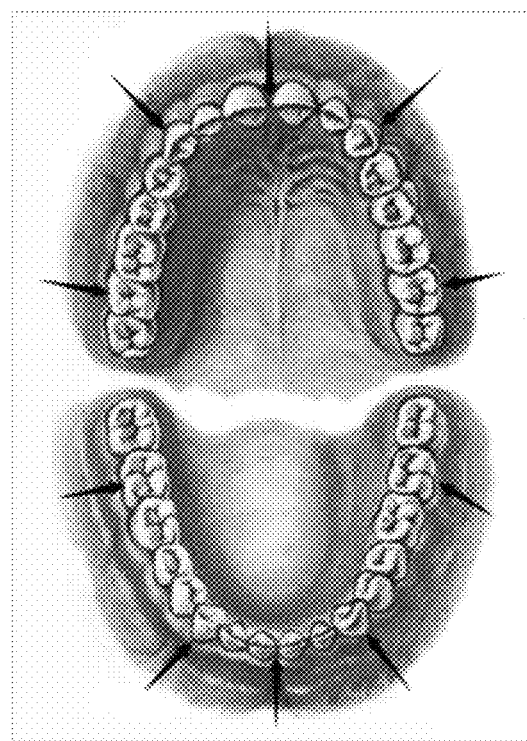
FIG. 2 shows five determined points to fit the dental arch convexity curve.
Figure 3:
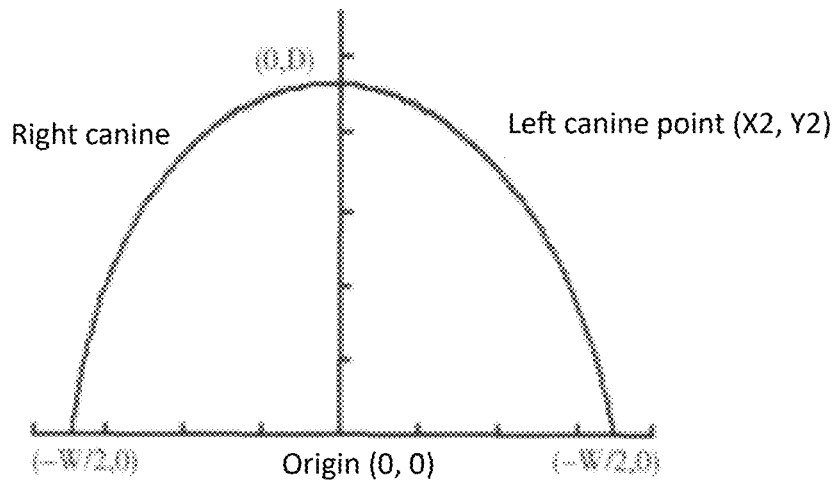
FIG. 3 shows a method of calculating a value of e in β function.

This step mainly comprises the following steps:

4.2.1) obtaining the buccal apex of incisor contact surface of the jaw where the abutment is, the point of bilateral canines with the maximum buccal curvature, and the point of bilateral second permanent molars with the maximum buccal curvature, with the five points as shown in FIG. 2;

4.2.2) determining β function according to the five points obtained in step 4.2.1) to fit the dental arch convexity curve. The formula of β function is shown as formula (2):

$$Y=D[1-(2X/W)^2]^e \quad \text{Formula (2)}$$

where: D is the width of the second permanent molar, that is, the distance between the points of bilateral second permanent molars with the maximum buccal curvature; W is the depth of the second permanent molar, that is, the distance between the connecting lines from the buccal apex of incisor contact surface to the point of bilateral second permanent molars with the maximum buccal curvature; e is determined by the position of canines, so that the distance from the curve to the point of bilateral canines with the maximum buccal curvature is the shortest and equal; the schematic diagram for calculating the value of e is shown in FIG. 3. Once D, W and e are calculated, the buccal dental arch convexity curve is determined;

4.2.3) repeating steps 4.2.1) and 4.2.2), and calculating the lingual dental arch convexity curve in the same manner.

Step 4 above may further comprise the following steps:

4.3) calculating the occlusal gum diameter height, calculating the distance from each point on the edge line to the occlusal plane according to the selected abutment edge line, and calculating the average distance as the occlusal gum diameter height, the specific calculation formula(s) being shown as Formulas (3) and (4):

$$d_i = \left| \frac{Ax_i + By_i + Cz_i + D}{\sqrt{A^2 + B^2 + C^2}} \right| \quad \text{Formula (3)}$$

where the equation of the occlusal plane is $Ax+By+Cz+D=0$, and the coordinate of the point on the abutment edge line is $(x_i, y_i, z_i)$;

$$d = \frac{1}{n}\sum_{i=1}^{n} d_i \qquad \text{Formula (4)}$$

where d is the calculated average distance, $d_i$ is the distance from a point on the abutment edge line to the occlusal plane, and n is the number of points on the abutment edge line; and 4.4) calculating the cusp pit and fissure ridge shape features of opposite jaws: calculating the occlusal surface features of the opposite jaw teeth according to the 3D model data of the upper jaw and lower jaw obtained in step 2.

This step mainly comprises the following steps:

4.4.1) interactively selecting the occlusal surface of the opposite jaw tooth; and 4.4.2) calculating the selected dental surface feature vector: first, obtaining the effective neighborhood around the cusp pit and fissure ridge in the occlusal surface according to the selection results; then establishing a local spherical coordinate system for the surface; next, calculating the elevation and azimuth of the normal at each vertex of the surface through the 2D histogram statistical method, and determining the position index in turn; finally, generating the maxillofacial feature vector (f1, f2, . . . , fn) of the opposite jaw tooth according to the 2D histogram.

Step 4 above may further comprise the following step:

4.5) data matching: matching the data of the to-be-produced tooth obtained previously with the data of the alternative dental crown in the database to quickly obtain a quasi-dental crown or bridge.

4.5.1) database establishment.

To facilitate the management of a standard tooth database, xml files may be used to store teeth, including tooth number, tooth type (single crown/crown bridge), tooth feature vector, and tooth storage path.

Figure 4:
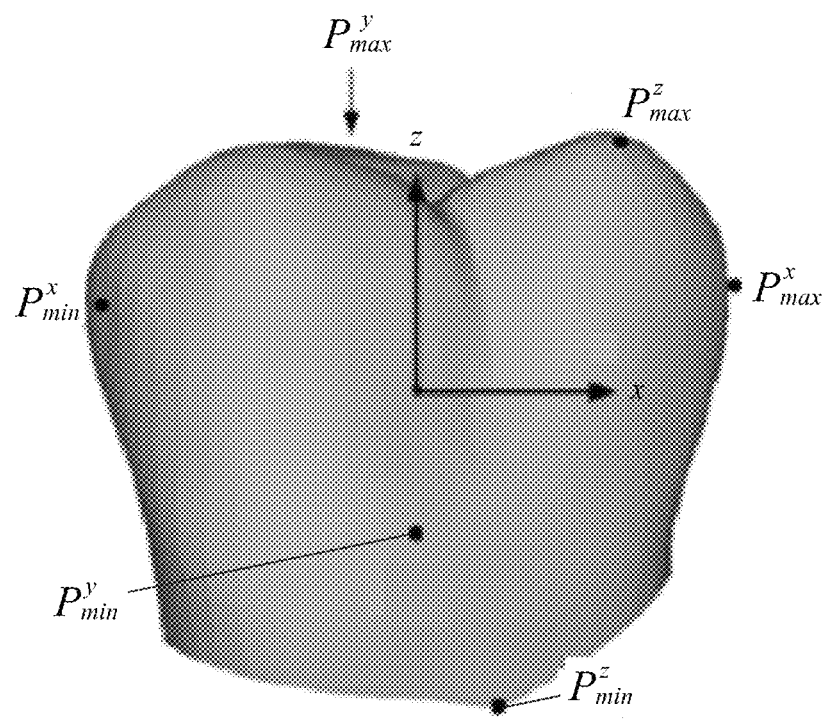
FIG. 4 shows 6 outline high points of the tooth model.
Figure 5:
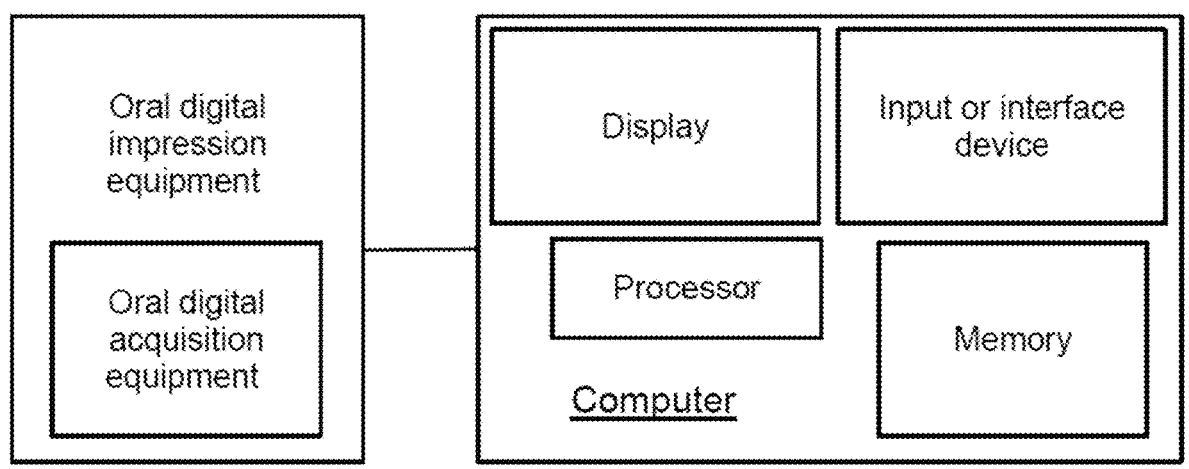
FIG. 5 shows an oral digital impression instrument, including oral digital acquisition equipment and a computer comprising a processor, a memory, a display and an input or interface device.

Six outline high points are obtained by calculating the coordinates of the tooth model. Two of the outline high points $P_{min}^{x}$ and $P_{max}^{x}$ are on the mesial and distal surfaces, two of the outline high points $P_{min}^{y}$ and $P_{max}^{y}$ are on the buccal and lingual surfaces, and two of the outline high points $P_{min}^{z}$ and $P_{max}^{z}$ are on the bottom and top surfaces, as shown in FIG. 4.

The coordinates of the six outline high points are recorded as $P_{min}^{x}(x_1,y_1,z_1)$, $P_{max}^{x}(x_2,y_2,z_2)$, $P_{min}^{y}(x_3,y_3,z_3)$, $P_{max}^{y}(x_4,y_4,z_4)$, $P_{min}^{z}(x_5,y_5,z_5)$, $P_{max}^{z}(x_6,y_6,z_6)$; the absolute value of the difference between x coordinates of the outline high points $P_{min}^{x}$ and $P_{max}^{x}$ is taken as the mesio-distal dimension, recorded as size_x; the absolute value of the difference between y coordinates of the outline high points $P_{min}^{y}$ and $P_{max}^{y}$ is taken as the buccolingual diameter, recorded as size_y; the absolute value of the difference between z coordinates of the outline high points $P_{min}^{z}$ and $P_{max}^{z}$ is used to limit the jaw-gum diameter, recorded as size_z; thus the calculation formula is shown as formula (5):

$$\text{size\_}x = |x_2 - x_1|$$

$$\text{size\_}y = |y_4 - y_3|$$

$$\text{size\_}z = |z_6 - z_5| \qquad \text{Formula (5)}$$

The overall size feature vector (size_x, size_y, size_z) of the alternative dental crown is obtained.

In the meantime, the cusp pit and fissure ridge feature vector (F1, F2, . . . , Fn) of the alternative dental crown is calculated by reference to 4.4.2), that is, the maxillofacial feature vector of the alternative dental crown.

Step 4.5) above may further comprise:

4.5.2) tooth number and tooth type matching: finding alternative dental crown data in the database according to the tooth number of the selected abutment and the selected dental crown type (single crown or crown bridge);

4.5.3) overall size matching: obtaining the feature vector (size_$x_0$, size_$y_0$, size_$z_0$) composed of three size parameters of the to-be-produced tooth from step 4.1)-step 4.4); the specific calculation method is shown as formula (5), and the overall size feature vector of the dental crown of the alternative dental crown can be calculated from step 4.1)-step 4.4) as (size_x', size_y', size_z'). The cosine of the included angle between the two vectors is calculated to measure the similarity between the feature vector of the to-be-produced tooth and the feature vectors of the alternative dental crown, and the cosine range of the included angle is [0,1]; the larger the cosine of the included angle, the smaller the included angle of the two vectors. When the directions of the two vectors coincide, the maximum cosine of the included angle is 1. The specific calculation formula of the cosine of the included angle is shown as formula (6):

$$\cos(\theta) = \frac{a \cdot b}{\|a\| \times \|b\|} = \frac{\sum_{i=1}^{n}(x_i \times y_i)}{\sqrt{\sum_{i=1}^{n}(x_i)^2} \times \sqrt{\sum_{i=1}^{n}(y_i)^2}}; \qquad \text{Formula (6)}$$

and 4.5.4) local feature matching: calculating the complementary vector (f1', f2', . . . , fn') of the maxillofacial feature vector (f1, f2, . . . , fn) of the opposite jaw tooth of the to-be-produced tooth, where (f1', f2', . . . , fn')= (−f1, −f2, . . . , −fn), and conducting local feature matching through calculating the cosine similarity of the vector (f1', f2', . . . , fn') and the cusp pit and fissure ridge feature vector (F1, F2, . . . , Fn) of the alternative dental crown.

Step 4 above may further comprise:

4.6) dental pattern adjustment: since the matched data should not fully meet the requirements, adjusting the tooth position according to the calculation results of 4.1), 4.2) and [3] 4.3);

4.6.1) integral adjustment: the three size parameters of the to-be-produced tooth are size_$x_0$, size_$y_0$ and size_$z_0$, and the three size parameters of the alternative dental crown are size_x', size_y' and size_z'. Suppose the scaling of the alternative dental crown in x, y and z directions as $s_x$, $s_y$ and $s_z$, the basic form of the homogeneous coordinate transformation matrix for scaling is as shown in formula (7):

$$S = \begin{bmatrix} s_x & 0 & 0 & 0 \\ 0 & s_y & 0 & 0 \\ 0 & 0 & s_z & 0 \\ 0 & 0 & 0 & 1 \end{bmatrix} \qquad \text{Formula (7)}$$

where the scaling is $s_x$, $s_y$ and $s_z$ respectively, obtained by the following formula (8):

$$s_x = size\_x_0/size\_x'$$

$$s_y = size\_y_0/size\_y'$$

$$s_z = size\_z_0/size\_z' \qquad \text{Formula (8)}$$

The alternative dental crown is scaled by virtue of the scaling matrix S, so that the size of the alternative dental crown is best fit.

4.6.2) occlusal surface adjustment: adjusting the normal vector of the occlusal surface of the alternative dental crown according to the maxillofacial feature vector of the opposite jaw tooth of the to-be-produced tooth to best fit;

4.6.3) adjusting the lower edge of the dental crown: adjusting the coordinates of each point on the lower edge of the dental crown according to the distance from each point on the abutment edge line to the occlusal plane calculated in step 4.3), so that the distance from each point on the lower edge of the dental crown to the highest point on the occlusal surface matches the distance from each point on the abutment edge line to the occlusal plane.

Data output 7: the designed tooth model being exported as a data format which can be imported by 3shape and EXOcad software.

The rapid intelligent design method of the present invention can be combined with the intraoral scanners and applied in the chair side design. When dentists finish the intraoral scan with the intraoral scanners, they can directly perform real-time design rapidly near the chair. Patients can observe the denture models immediately, thus improving the patients' experience. The data acquisition, data preprocessing and intelligent design steps can also be integrated into the intraoral scanner. After the intraoral scanner completes a preliminary design, the data is transmitted to the design computer beside the dental chair. The dentists can carry out secondary manual design according to the actual inspection, and then conduct quick matching in the database to accelerate the denture (e.g., dental crown or dental bridge) design.

The above embodiments are preferred embodiments. It should be pointed out that the above preferred embodiments should not be regarded as the limitation to the present invention, and the protection scope of the present invention should be subject to the scope defined in the claims. For those skilled in the art, some improvements and modifications can be also made without departing from the spirit and scope of the present invention, and these improvements and modifications shall be deemed as in the protection scope of the present invention.

What is claimed is:

1. A method of modeling and/or designing a dental crown of a to-be-produced tooth using an oral digital impression instrument, comprising:
    a) storing data of alternative dental crowns in a database accessible by a computer operatively connected to the oral digital impression instrument, the alternative dental crown data including a tooth number, a dental crown type, an overall size feature vector of the dental crown, and a storage path of at least one tooth;
    b) acquiring 3D data of teeth and/or an oral cavity of a patient with oral digital acquisition equipment of the oral digital impression instrument and generating a 3D model of the teeth and/or the oral cavity, the 3D data including an upper jaw and a lower jaw, and confirming occluding relations between the upper jaw and the lower jaw;
    c) labeling the 3D model, an abutment tooth position, the dental crown type and an abutment edge line;
    d) automatically processing a design of the to-be-produced tooth according to the labeled 3D model, and matching a plurality of the alternative dental crowns from the database;
    e) obtain the overall size feature vector of the dental crown by calculation using a six-point method, the six-point method comprising obtaining six outline high points through maximum and minimum tooth crown coordinates, of which two outline high points of mesial and distal surfaces are $P_{min}^x$ and $P_{max}^x$, two additional outline high points of buccal and lingual surfaces are $P_{min}^y$ and $P_{max}^y$, two further outline high points of bottom and top surfaces are $P_{min}^z$ and $P_{max}^z$, the overall size feature vector of the dental crown is (size_x, size_y, size_z), size_x is an absolute value of a difference between x coordinates of the outline high points $P_{min}^x$ and $P_{max}^x$, size_y is an absolute value of a difference between y coordinates of the outline high points $P_{min}^y$ and $P_{max}^y$, and size_z is an absolute value of a difference between z coordinates of the outline high points $P_{min}^z$ and $P_{max}^z$;
    f) determining a similarity between the plurality of alternative dental crowns and the to-be-produced tooth according to a cosine of an included angle between an overall size feature vector of at least one of the plurality of alternative dental crowns and the overall size feature vector of the dental crown, the cosine of the included angle being [0,1];
    g) adjusting a maxillofacial feature vector and the at least one of the plurality of alternative dental crowns according to a scaling of an overall size feature vector of the to-be-produced tooth; and
    h) exporting the design of the to-be-produced tooth according to the labeled 3D model.

2. The method according to claim 1, wherein the overall size feature vector of the to-be-produced tooth as (size_$x_0$, size_$y_0$, size_$z_0$), the overall size feature vector of the alternative dental crown(s) as (size_x', size_y', size_z'), and a scaling of the alternative dental crown in x, y and z directions is $s_x$, $s_y$ and $s_z$ respectively, where:

$$s_x = size\_x_0/size\_x'$$

$$s_y = size\_y_0/size\_y'$$

$$s_z = size\_z_0/size\_z'.$$

3. An oral digital impression instrument, comprising:
    oral digital acquisition equipment, configured to scan an oral cavity of a patient and obtain three-dimensional (3D) data of teeth in the oral cavity, and
    a computer comprising a processor, a memory, a display and an input or interface device, the memory storing therein a non-transitory set of instructions which, when executed by the processor, is configured to:
    a) store alternative dental crown data in an xml file, the alternative dental crown data including a tooth number, a dental crown type, an overall size feature vector of a dental crown, and a storage path of at least one of the teeth;
    b) acquire the 3D data of the teeth and/or the oral cavity with the oral digital acquisition equipment and generate a 3D model of the teeth and/or the oral cavity, the 3D data including an upper jaw and a lower jaw, and confirming occluding relations between the upper jaw and the lower jaw;

c) label the 3D model, an abutment tooth position, the dental crown type and an abutment edge line;

d) automatically process a design of a to-be-produced tooth according to the labeled 3D model, and match a plurality of alternative dental crowns from a database;

e) obtain the overall size feature vector of the dental crown by calculation using a six-point method, the six-point method comprising obtaining six outline high points through maximum and minimum tooth crown coordinates, of which two outline high points of mesial and distal surfaces are $P_{min}^x$ and $P_{max}^x$, two additional outline high points of buccal and lingual surfaces are $P_{min}^y$ and $P_{max}^y$, two further outline high points of bottom and top surfaces are $P_{min}^z$ and $P_{max}^z$, the overall size feature vector of the dental crown is (size_x, size_y, size_z), size_x is an absolute value of a difference between x coordinates of the outline high points $P_{min}^x$ and $P_{max}^x$, size_y is an absolute value of a difference between y coordinates of the outline high points $P_{min}^y$ and $P_{max}^y$, and size_z is an absolute value of a difference between z coordinates of the outline high points $P_{min}^z$ and $P_{max}^z$ f) determine a similarity between the plurality of alternative dental crowns and the to-be-produced tooth according to a cosine of an included angle between an overall size feature vector of at least one of the plurality of alternative dental crowns and the overall size feature vector of the dental crown, the cosine of the included angle being [0,1];

g) adjust a maxillofacial feature vector and the at least one of the plurality of alternative dental crowns according to a scaling of an overall size feature vector of the to-be-produced tooth; and h) export the design of the to-be-produced tooth according to the labeled 3D model.

4. The oral digital impression instrument according to claim 3, wherein the set of instructions, when executed by the processor, is configured to acquire the 3D data of the teeth and/or the oral cavity with the oral digital acquisition equipment and generate the 3D model of the teeth and/or the oral cavity by acquiring 3D model data of the upper jaw and the lower jaw and buccal data at an occlusion, respectively.

5. The oral digital impression instrument according to claim 4, wherein the set of instructions, when executed by the processor, is further configured to acquire the 3D data of the teeth and/or the oral cavity with the oral digital acquisition equipment and generate the 3D model of the teeth and/or the oral cavity by calculating and fixing a contact relation between 3D models of the upper jaw and the lower jaw through the buccal data.

6. The oral digital impression instrument according to claim 5, wherein the set of instructions, when executed by the processor, is further configured to acquire the 3D data of the teeth and/or the oral cavity with the oral digital acquisition equipment and generate the 3D model of the teeth and/or the oral cavity by manually translating and rotating the 3D models of the upper jaw and the lower jaw in a 3D coordinate system, so that the 3D models of the upper jaw and the lower jaw are in a correct occluding relation.

7. The oral digital impression instrument according to claim 4, wherein the set of instructions, when executed by the processor, is configured to automatically process the design of the to-be-produced tooth by:

a) calculating a distance between adjacent teeth;
b) calculating buccal and lingual dental arch convexity curves;
c) calculating an occlusal gum diameter height; and
d) calculating a cusp pit and fissure ridge shape features of the upper jaw and the lower jaw.

8. The oral digital impression instrument according to claim 7, wherein the set of instructions, when executed by the processor, is further configured to:

a) interactively select two points closest to the adjacent teeth on the abutment edge line, and calculate a distance between these two points to obtain the distance between the adjacent teeth;

b) fit a dental arch convexity curve by a method based on a β function according to the 3D model data of the upper jaw and the lower jaw;

c) calculate a distance from each point on the abutment edge line to an occlusal plane according to the abutment edge line, calculate an average distance, and consider the average distance to be an occlusal gum diameter height; and d) calculate occlusal surface features of the teeth according to the 3D model data of the upper jaw and lower jaw.

9. The oral digital impression instrument according to claim 8, wherein calculating the buccal and lingual dental arch convexity curves comprises:

a) obtaining a buccal apex of an incisor contact surface of a jaw containing the abutment, a point of bilateral canines with a first maximum buccal curvature, and a point of bilateral second permanent molars with a second maximum buccal curvature;

b) determining the β function according to the buccal apex, the point of bilateral canines, and the point of bilateral second permanent molars to fit the dental arch convexity curve; and c) calculating the buccal and lingual dental arch convexity curves from the β function and the dental arch convexity curve.

10. The oral digital impression instrument according to claim 8, wherein calculating the cusp pit and the fissure ridge shape features of the upper jaw and the lower jaw comprises:

a) interactively selecting an occlusal surface of an opposite jaw tooth; and b) obtaining an effective neighborhood around the cusp pit and a fissure ridge in the selected occlusal surface, then establishing a local spherical coordinate system for the selected occlusal surface; calculating an elevation and an azimuth of a normal at each vertex of the selected occlusal surface using a 2D histogram statistical method, and determining a position index; then generating a maxillofacial feature vector (f1, f2, ..., fn) of the opposite jaw tooth according to the 2D histogram statistical method.

11. The oral digital impression instrument according to claim 10, wherein the set of instructions, when executed by the processor, is configured to determine the similarity between the at least one of the plurality of alternative dental crowns and the to-be-produced tooth by:

a) matching the tooth number and dental crown type;
b) matching an overall size; and
c) matching local features.

12. The oral digital impression instrument according to claim 11, wherein:

a) matching the tooth number and the dental crown type comprises finding alternative dental crown data in the database according to a tooth number of a selected abutment and the dental crown type;
b) matching the overall size comprises calculating the overall size feature vector of the to-be-produced tooth as (size_$x_0$, size_$y_0$, size_$z_0$) and the overall size feature vector of the alternative dental crown(s) as (size_x', size_y, size_z'), and determining a similarity between the alternative dental crown(s) and the to-be-produced tooth according to the cosine of the included angle; and
c) matching local features comprises calculating a complementary vector (f1', f2', . . . , fn') of an occlusal surface feature vector (f1, f2, . . . , fn) of a tooth opposite from the to-be-produced tooth, the complementary vector (f1', f2', . . . , fn')=(−f1, −f2, . . . , −fn), and calculating a cosine similarity of the complementary vector (f1', f2', . . . , fn') and a maxillofacial feature vector of the alternative dental crown(s).

13. The oral digital impression instrument according to claim 8, wherein the set of instructions, when executed by the processor, is configured to adjust the maxillofacial feature vector and the at least one of the plurality of alternative dental crowns by:
a) adjusting an integral using a scaling matrix S according to the overall size feature vector of the to-be-produced tooth and a scaling of the at least one of the plurality of alternative dental crowns, in a manner ensuring an optimal size matching of the at least one of the plurality of alternative dental crowns;
b) adjusting a normal vector of a dental surface of the at least one of the plurality of alternative dental crowns according to a maxillofacial feature vector of a tooth opposite from the to-be-produced tooth; and
c) adjusting coordinates of each point on a lower edge of the at least one of the plurality of alternative dental crowns according to a distance from each point on the abutment edge line to the occlusal plane, so that the distance from each point on the lower edge of the at least one of the plurality of alternative dental crowns to a highest point on the occlusal surface matches a distance from each point on the abutment edge line to the occlusal plane.

14. The oral digital impression instrument according to claim 3, wherein the set of instructions, when executed by the processor, is configured to label the 3D model, the abutment tooth position, the dental crown type and the abutment edge line by:
a) selecting an abutment, highlighting the abutment, and recording the tooth number and/or a tooth position, the abutment having the dental crown type;
b) selecting the dental crown type as a single crown or a crown bridge; and
c) marking edge lines interactively.

15. The oral digital impression instrument according to claim 14, wherein the tooth number and/or the tooth position is given or defined by a Federation Dentaire Internationale (FDI) notation, and marking edge lines interactively comprises selecting points of triangular mesh on an edge line of the abutment, sketching points of the edge line of the abutment one by one, and highlighting a final edge line with a color.

16. The oral digital impression instrument according to claim 14, wherein when the dental crown type is a single crown, recording the tooth number of the abutment; and when the dental crown type is a crown bridge, recording the tooth number of each of leftmost and rightmost abutments of the crown bridge and the tooth number of each to-be-produced tooth in the crown bridge.

17. The oral digital impression instrument according to claim 3, wherein the oral digital acquisition equipment comprises an intraoral scanner.

18. The oral digital impression instrument according to claim 3, wherein the overall size feature vector of the to-be-produced tooth as (size_$x_0$, size_$y_0$, size_$z_0$), the overall size feature vector of the alternative dental crown(s) as (size_x, size_y, size_z'), and a scaling of the alternative dental crown in x, y and z directions is $s_y$, $s_y$ and $s_z$ respectively, where:

$s_x$=size_$x_0$/size_$x'$ $s_y$=size_$y_0$/size_$y'$ $s_z$=size_$z_0$/size_$z'$.

* * * * *